United States Patent
Knüttel

(10) Patent No.: US 6,185,445 B1
(45) Date of Patent: Feb. 6, 2001

(54) MR TOMOGRAPH COMPRISING A POSITIONING SYSTEM FOR THE EXACT DETERMINATION OF THE POSITION OF A MANUALLY GUIDED MANIPULATOR

(75) Inventor: Bertold Knüttel, Rheinstetten (DE)

(73) Assignee: Bruker Medizintechnik GmbH, Rheinstetten (DE)

( * ) Notice: Under 35 U.S.C. 154(b), the term of this patent shall be extended for 0 days.

(21) Appl. No.: 09/120,321

(22) Filed: Jul. 22, 1998

(30) Foreign Application Priority Data

Jul. 30, 1997 (DE) .............................. 197 32 784

(51) Int. Cl.[7] .................................. A61B 17/00
(52) U.S. Cl. ............................................. 600/411
(58) Field of Search ................... 600/439, 124; 601/2; 602/3; 603/4; 606/130

(56) References Cited

U.S. PATENT DOCUMENTS

| | | | |
|---|---|---|---|
| 5,060,650 | * 10/1991 | Wurster et al. | 600/439 |
| 5,152,289 | * 10/1992 | Viebach et al. | 600/439 |
| 5,168,211 | 12/1992 | Laukien et al. | 324/319 |
| 5,399,146 | * 3/1995 | Nowacki et al. | 600/439 |
| 5,414,360 | 5/1995 | Westphal et al. | 324/318 |
| 5,463,364 | 10/1995 | Müller | 335/299 |
| 5,545,997 | 8/1996 | Westphal et al. | 324/320 |
| 5,570,073 | 10/1996 | Müller | 335/299 |
| 5,647,361 | 7/1997 | Damadian . | |
| 5,703,922 | * 12/1997 | Rattner | 600/439 |

FOREIGN PATENT DOCUMENTS

| | | |
|---|---|---|
| 4029477 | 6/1994 | (DE) . |
| 0640842 | 3/1995 | (EP) . |
| 0 728 446 A1 | 8/1996 | (EP) . |
| 0 757 255 A2 | 2/1997 | (EP) . |
| WO96/31753 | 10/1996 | (WO) . |

OTHER PUBLICATIONS

Company brochure "VectorVision: The power of unlimited surgical tracking", BrainLAB, (1996).

H.U. Lemke et al.: Computer Assisted Radiology, pp. 751–756 (1996) "Real–Time Volume Visualization of Mecial Image . . . " by Hübner et al.

U. Kühnapfel et al.: "The Karlsruhe Endoscopic Surgery Trainer as an example for Virtual Reality in Medical Education".

D. Glauser et al.: "Neurosurgical Robot Minerva. First Results and Current Developments".

Leaflet Halte—und Führungssystem für die endoskopische Chirurgie, "C–Bogen" issued by Forschungszentrum Karlsruhe, Germany.

IEEE Engineering in Medicine and Biology, "Stereotactic Brain Surgery", May/Jun. 1995, pp. 314–317.

* cited by examiner

Primary Examiner—Marvin M. Lateef
Assistant Examiner—Maulin Patel
(74) Attorney, Agent, or Firm—Paul Vincent

(57) ABSTRACT

An MR tomograph, the magnet system (2) and gradient system of which permit access to the investigation volume along at least two essentially orthogonal axes, comprises a positioning system for the exact determination of the position of a manually guided manipulator (12) relative to the measuring object (6) which is investigated by means of imaging MR measurement and located in the investigation volume (3) of the MR tomograph (1); with a mounting frame (11) with which the manipulator (12) is connected via movable mechanics comprising a measuring means through which the respective spatial position of the manipulator (12) relative to the mounting frame (11) can be determined, wherein the measuring means of the movable mechanics does not utilize any MR signals and wherein the measured position of the manipulator (12) is displayed on the MR image. In this way, minimum-invasive operations, e.g. by means of a biopsy needle, can be carried out manually and the position of the manipulator, used in this connection, within the measuring object can be monitored by means of simultaneously recorded MR slice images during the operation and can be corrected, if necessary.

21 Claims, 2 Drawing Sheets

MR TOMOGRAPH COMPRISING A POSITIONING SYSTEM FOR THE EXACT DETERMINATION OF THE POSITION OF A MANUALLY GUIDED MANIPULATOR

This application claims Paris Convention Priority of German Patent application No. 19732784.2 filed Jul. 30, 1997 the complete disclosure of which is hereby incorporated by reference.

BACKGROUND OF THE INVENTION

The invention concerns an MR tomograph, having a magnet system for generating a homogeneous magnetic field within a volume to be investigated and a gradient system for generating magnetic gradient fields which vary linearly in the volume to be investigated, wherein the magnet system and the gradient system permit access to the volume to be investigated along at least two axes, which intersect at an essentially right angle; a radio frequency (RF) transmitting and receiving system for irradiating RF pulses onto a measuring object to be investigated within the investigation volume and for receiving MR signals from the measuring object; and also an evaluation and display means for generating and displaying an MR image from the inside of the measuring object.

MR tomographs offering the possibility to insert the measuring object, in particular a patient, into the investigation volume, not only from an axial but also from a transverse direction are known e.g. from U.S. Pat. No. 5,168,211. Further developments of such MR tomographs offering the surgeon in charge sufficient transverse access to the investigation volume, which can be utilized e.g. for carrying out minimum-invasive operations with simultaneous monitoring of the operation via simultaneously generated MR slice images, are known e.g. from DE 40 29 477 A1, U.S. Pat. No. 5,414,360, U.S. Pat. No. 5,463,364 or U.S. Pat. No. 5,545,997, where various geometrical configurations of magnet systems and gradient systems are described which permit such transverse access to the investigation volume.

U.S. Pat. No. 5,570,073 describes a further possibility of almost lateral access to the investigation volume in addition to the axial access and shows an MR disk coil which is designed particularly compact in the axial direction such that access to the investigation volume at a relatively large angle with respect to the axis of the configuration is possible. Thus, minimum-invasive surgical treatment with simultaneous recording of MR slice images becomes also possible.

A further feasible possibility for a tomography system with lateral access to the homogeneity volume is a so-called "inside-out" arrangement in which the homogeneity volume is arranged outside of the actual tomograph owing to the particular construction of the magnet system. Such an arrangement is described e.g. in DE 296 09 289.4 U.

With respect to the above-mentioned minimum-invasive operations which can be carried out e.g. by means of a biopsy needle, it is furthermore known to provide a computer tomography (CT) image or an MRI image in the background. Up to now, said tomogram or projected image has been obtained previously, i.e. before the patient (or the object to be investigated) is removed from the tomograph, and then the operation is carried out outside of the tomograph, in particular outside of the investigation volume. In this connection, freely movable biopsy needles, provided with marking points (see e.g. the leaflet "VectorVision" by the company BrainLAB, Heimstetten, September 1996) and also stationary positioning systems (e.g. magazine article by Hübner and Kühnapfel in Computer assisted Radiologie, 751–756, 1996) are used, wherein the mounting of the biopsy needle is displaceable in a manner defined by two circles and the needle is insertable in a defined manner. The position of the freely movable needle is determined optically e.g. by means of reflecting, simultaneously moving spheres (see leaflet "VectorVision"). The position of the needle is faded into the image which has been recorded previously at another location. In this connection, it is of course necessary to make sure that the coordinate systems coincide as exactly as possible in each case. This is probably achieved by means of defined mechanical strokes. In this connection, it seems to be absolutely necessary that the investigation object is positioned precisely and remains in place. For this purpose further optical marking points are stuck onto the object, if necessary.

The known biopsy methods with a "free" needle have the disadvantage that, during biopsy, the needle remains steady only to such an extent as provided by the hand of the surgeon guiding the needle. It is difficult to use the known methods having optical marking points in the inside of a tomography magnet system for on-line examinations since owing to the still confined circumstances and predetermined bedding, there are some obstacles in the way which block off the light, let alone the patient herself/himself or the person guiding the manipulator. For this reason, the defined manually guided manipulators which are mounted e.g. on a stereo-tactic ring have been used up to now only outside of the tomograph, or outside of its investigation volume having a homogeneous magnetic field.

On the other hand, when the operation is carried out outside of the imaging apparatus, the position of an inner location which is the object of the operation (e.g. in the brain, kidney, mamma etc.) can be different from its position during imaging. It is possible that an organ of the patient was moved owing to the transport, a biopsy needle used for the operation may displace tissue, a blood vessel may have changed its spatial position owing to pulsation etc. The absolute position of the manipulator is then possibly shown shifted by a few millimeters with respect to the real position such that the operation may not have the desired success or might even be lethal for the patient.

In the above-mentioned article by Hübner and Kühnapfel it is generally said that the apparatus described therein offers the possibility of simultaneous diagnosis and on-line three-dimensionally based guiding assistance during surgical operations, however use of an MR tomograph offering transverse or at least angular lateral access is not mentioned therein and the operation is not carried out manually by a surgeon either. They rather suggest a "biopsy robot" which is supposed to carry out biopsy fully automatically, and if possible also via remote control, within a conventional tomograph without lateral accessibility.

Irrespective of the fact that systems of this kind do not yet exist concretely and are not used in practice, they would have the considerable disadvantage that such a robot configuration would have to be equipped with some kind of a motor which would undoubtedly comprise ferromagnetic parts which would impair to a considerable extent the homogeneity of the magnetic field in the investigation volume containing the robot. This would eventually cause the quality of the images of the MR tomograms obtained to be too bad to be useful for exact positioning of the biopsy needle. This might also be the reason why the biopsy robot apparatus suggested in theory in the above-mentioned magazine article by Hübner and Kühnapfel has not yet been realized in an MR tomograph.

SUMMARY OF THE INVENTION

In contrast thereto, it is the object of the invention to provide an MR tomograph having the initially described features which allows minimum-invasive operations to be carried out manually, e.g. by means of a biopsy needle, observation of the position of the manipulator used in the inside of the measuring object by means of simultaneously recorded MR slice images during the operation and possibly correction thereof.

According to the invention, this object is achieved by an MR tomograph having the initially described features, comprising a positioning system for the exact determination of the position of a manually guided manipulator, in particular the tip of a biopsy needle, relative to the measuring object, in particular head or extremities of a patient, which is investigated by means of imaging MR-measurements and contained in the investigation volume of the MR tomograph, comprising a mounting frame to which the manipulator is connected via movable mechanics which comprise a measuring means via which the respective spatial position of the manipulator with respect to the mounting frame can be detected, wherein the measuring device of the movable mechanics does not necessarily use MR signals, and wherein the measured position of the manipulator is displayed on the MR image.

By means of such MR tomographs, manual on-line examinations or operations can be carried out with simultaneous monitoring of the manipulation on MRI images. In contrast to the theoretically proposed use of a "biopsy robot", limitations of the homogeneity of the magnetic field in the investigation volume have not to be expected, however, sufficient transverse access to the investigation volume must be possible.

One embodiment of the inventive MR tomograph is particularly preferred, in which the mounting frame is provided with at least one marking point which is located within the investigation volume in which the magnetic field is homogeneous and the gradient fields are linear, and contains a substance in which measurable MR signals can be excited which define the spatial position of the mounting frame in the MR image via the imaging MR measurement.

In contrast to indirect methods in which the determination of the position is effected e.g. via IR optical measurements at the mounting frame and with marking points mounted to the patient (e.g. spheres) by calculating the movement of the spheres, the determination of the position can be effected directly via the MRI image through the use of an MR measurable substance in a marking point. This is also advantageous with respect to methods wherein the manipulator, e.g. the tip of a biopsy needle, is accommodated in the measuring object during the operation by means of the MR slice image, since the manipulators contain as a rule metal-conducting material which can cause image artifacts and distortions exactly at the interesting location in the measuring object. The images generated in this connection, e.g. of a biopsy needle in the tissue to be investigated or treated, are moreover very blurred since the needle itself does not emit any actual MR signals but merely causes image disturbances and thus is shown as a shadow whose spatial allocation cannot be defined exactly.

An improvement of the above embodiment is particularly preferred wherein the evaluation means—or a computer connected thereto—can determine by calculation the position of the manipulator in the MR image—in particular that of a biopsy needle tip from the mounting frame position, which was determined by an MRI measurement, and from the relative position of the manipulator, which was determined by the measuring device without an MR measurement. Instead of a determination of the relative position inside the object—possibly giving rise to large errors due to gradient errors as well as to tissue displacements by the manipulator, due to pulsating vessels, etc., such that the absolute position of e.g. a biopsy needle may possibly be improperly determined by several millimeters. Due to the MR image of the marking point fixed to the mounting frame with the configuration according to the invention the position of the manipulator can—without large technical effort—be calculated within an accuracy of better than a millimeter relative to the mounting frame position—which in its turn can be determined very precisely—and the manipulator position can therefore be displayed in the MR image with a positional precision relative to the surrounding tissue with an order of magnitude which is also less than a millimeter.

It is preferred that the MR measurable substance inside the marking point contains protons, in particular water, since usually MRI images of biological measuring objects are obtained via nuclear magnetic resonance of protons.

It is preferred that the MR measurable substance is in the form of a gel which can be kept in an easy and leak-proof manner in e.g. a capsule of synthetic material.

In a particularly preferred manner, the entire positioning system consists exclusively of non-magnetic materials such that there is no danger of impairing the homogeneity of the magnetic field in the investigation volume.

In a preferred embodiment of the inventive MR tomograph, further orientation aid is provided through which the spatial position of the manipulator relative to the mounting frame can be determined by means of mechanical, electrical, piezoelectrical or optical path length measurements. Sensors for such path length measurements having a degree of accuracy better than one millimeter are easily commercially available.

It is preferred to provide a marking point, comprising an MR measurable substance, which is rigidly connected to the measuring object. In this way it is possible to determine the absolute position of the measuring object itself via MRI images and compare it with the absolute position of the mounting frame.

A further improvement of the invention is particularly preferred wherein the marking point which is mechanically fixed to the mounting frame is identical with the marking point which is rigidly connected to the measuring object, such that a comparison of the relative positions can be omitted.

A further advantageous embodiment of the invention is characterized in that a means for mechanical guidance of the manipulator is provided covering a range of solid angle and for determination of the respective spatial angular position of the manipulator.

In a further improvement of this embodiment, the means for mechanical guidance of the manipulator comprise a gimbal mounting such that any spatial coordinates of the manipulator position can be easily approached.

Preferably, the mounting frame can be displaced along two circular arcs which are essentially perpendicular on top of each other.

In a further, particularly preferred embodiment of the invention, a device for the determination of the respective axial position of the manipulator relative to the guiding means is provided. Thus, it is possible to determine the depth of insertion of the applied biopsy needle exactly at any time of the operation.

Furthermore, the means for mechanical guidance of the manipulator may also comprise a ball joint to enable tilting movements of the manipulator.

In a further improvement of this embodiment, the manipulator comprises a biopsy needle which is pivotable, usually by relatively small angles, in a defined manner about a point located preferably close to the surface of the measuring object. In addition to the movement about the three main coordinates (e.g. position on two orthogonal arcs of a circle and also axial depth of insertion) the biopsy needle can be tilted to a minimum extent about a fixed injection point, e.g. a hole in the cranium of a patient during brain surgery. It is clear that this degree of freedom, when permitted has to be permanently measured and displayed to provide the surgeon at any time with exact information about the actual position of the tip of the biopsy needle or of another manipulation device.

In another advantageous further improvement of the invention, a marking point comprising MR measurable substance is mechanically rigidly connected to the guiding means or the guiding means contain an MR measurable substance. Thereby, the position of the manipulator itself can be determined also via MR measurement.

A method of operating an MR tomograph according to the invention with a stereo-tactic positioning system lies also within the scope of the present invention, wherein the absolute position of the mounting frame is determined simultaneously during actuation of the manipulator through imaging MR measurements on the basis of measuring signals from the marking point comprising MR measurable substance.

A particularly preferred embodiment of the inventive method is characterized in that the relative position of the manipulator with respect to the mounting frame is permanently determined simultaneously during actuation of the manipulator relying on mechanical, electrical, piezoelectrical or optical measuring signals of corresponding marking points.

In a particularly advantageous further improvement, the absolute position of a certain portion of the manipulator, e.g. the top of the needle which is inside the measuring object during manipulation, is determined via computer calculation and is faded into the recorded MR image.

Also within the scope of the invention is a method of guiding the tip of an e.g. biopsy needle to a predetermined point inside an object in the MR tomograph according to the invention, wherein the biopsy needle can be guided in a defined manner on two circular arcs outside of the measuring object and be displaced in a defined manner along an axis which is essentially perpendicular to the circular arcs, comprising the following method steps:

a) the biopsy needle is at first outside of the measuring object, b) an MR image of the measuring object is gained and displayed, c) a desired position is marked on said MR image, preferably via a mouse click, d) the evaluation and display means determines optimum coordinates along the circular arcs and the axis, e) deviations from these are faded into the MR image, preferentially graphically, and are permanently updated, f) the displayed deviations along the circular arcs are minimized manually and the position thus found is fixed along the circular arcs, g) the deviation along the axis is minimized by manually introducing the biopsy needle into the measuring object along the axis, thus taking into consideration the permanently displayed and updated deviation until the tip of the biopsy needle has reached the predetermined point.

Thereby, it is advantageous to support the graphical display by an acoustic display.

Further advantages of the invention can be derived from the description and the drawing. The features mentioned above and below may also be applied in accordance with the invention individually or in any arbitrary combination. The embodiments shown and described are not to be understood as exhaustive enumeration but rather have exemplary character for describing the invention.

The invention is shown in the drawing and is further explained by means of embodiments. In the drawing:

DESCRIPTION OF THE PREFERRED EMBODIMENT

Figure 1:
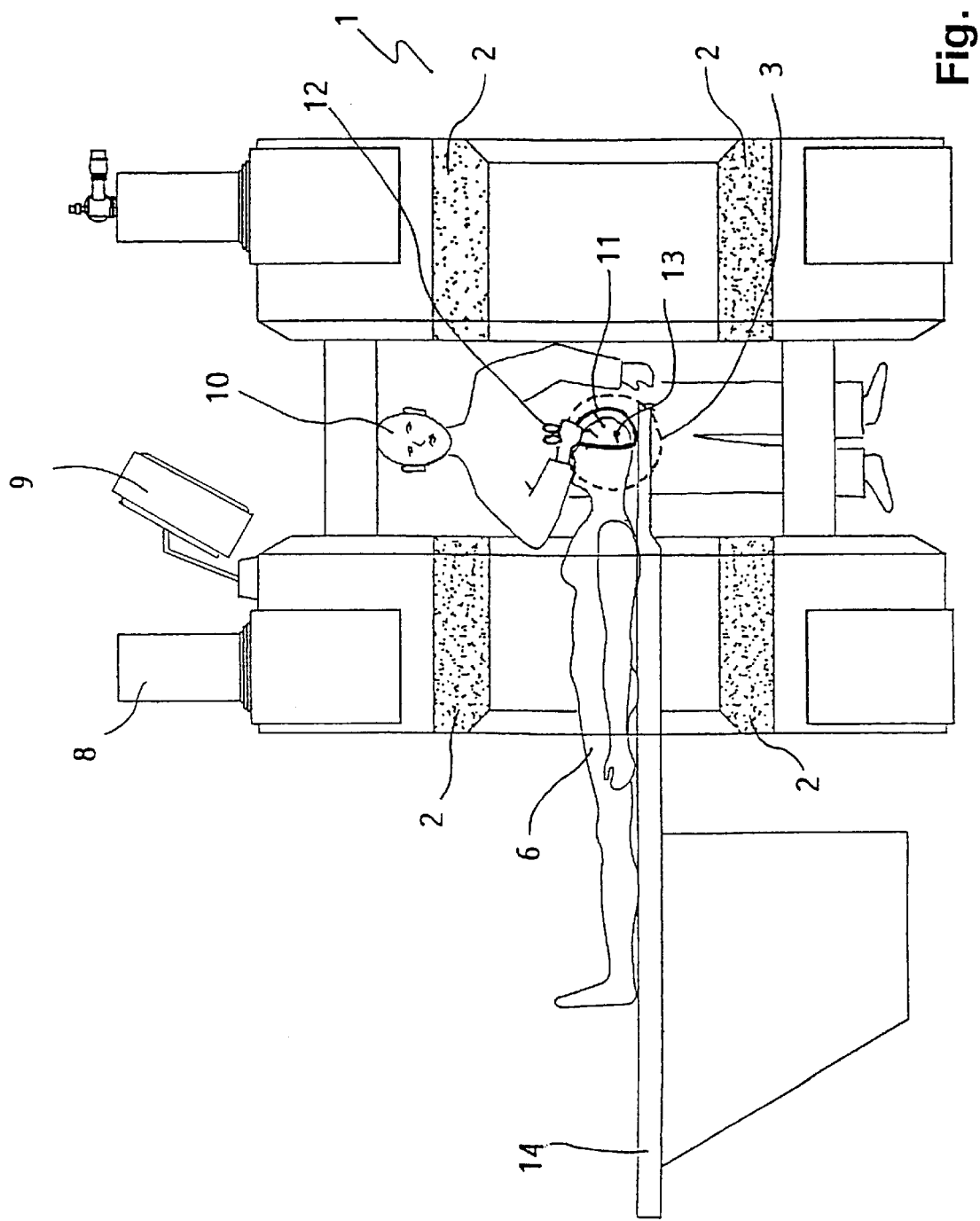
FIG. 1 shows a schematic vertical sectional view of an MR tomography system, the patient and surgeon being indicated.

The MR tomograph 1 schematically shown in the vertical lateral sectional view of FIG. 1 generates a homogeneous magnetic field in an investigation volume 3 by means of a magnet system 2 which may be constructed e.g. from wound magnetic coils and/or permanent magnetic elements like rings and the like. Furthermore, the MR tomograph 1 comprises a gradient system which can generate linearly varying magnetic gradient fields in the investigation volume 3. Finally, a radio frequency transmitting and receiving system is provided for irradiating RF pulses onto a measuring object 6 to be investigated in the investigation volume 3 and for receiving MR signals from the measuring object 6. The MR tomograph 1 comprises also an evaluation means 8 and a display means 9 for generating and displaying an MR image from the inside of the measuring object 6. It is essential for the inventive MR tomograph 1 that the magnet system 2, the gradient system 4 and the RF transmitting and receiving system 5 are constructed such that access to the investigation volume 3 in the axial direction on the one hand and on the other hand in a direction perpendicular thereto is possible. In this manner, a surgeon 10 can easily reach the patient, i.e. the measuring object 6, resting on the patient bed 14 in order to examine or operate on the patient during MR measurement, in the shown case a minimum-invasive operation on the brain of the patient.

Figure 2:
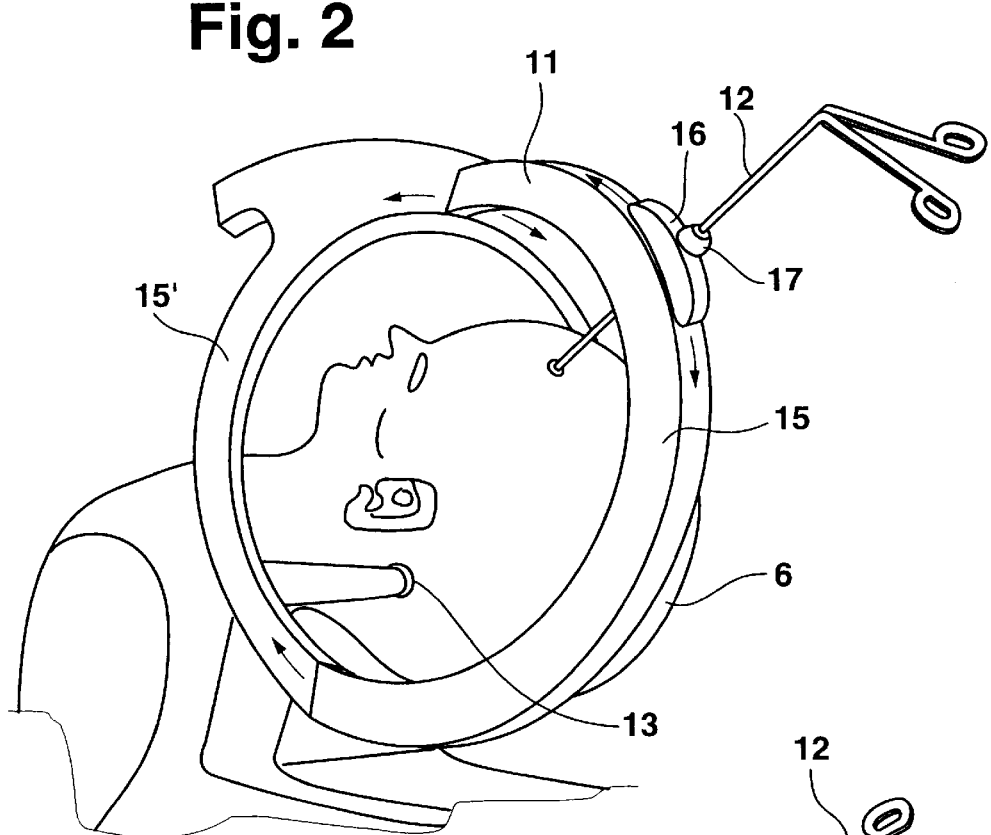
FIG. 2 a stereo-tactic positioning system for the exact determination of the position of a manipulator as part of the inventive MR tomograph.

For this purpose a stereo-tactic positioning system is provided for the exact determination of the position of a manually guided manipulator 12, the end of which is provided with e.g. the tip of a biopsy needle. The part of the body located in the investigation volume 3, e.g. the head of the patient is mechanically tightly connected with a mounting frame 11 which again is connected to the manipulator 12 via movable mechanics (FIG. 2). Said movable mechanics comprise a measuring means via which the respective spatial position of the manipulator 12 with respect to the mounting frame 11 can be determined.

For determination of the position of the mounting frame 11 in relation to the measuring object 6, at least one marking point 13 (see also FIG. 2) is rigidly connected with the mounting frame 11 and preferably also with the measuring object 6. This marking point 13 contains a substance in which measurable MR signals can be excited which define, via imaging MR measurements, the spatial position of the mounting frame in an MR slice image recorded by the measuring object 6. The evaluation means 8 is then able to determine, on the basis of the signals received from the measuring means, the relative position of the manipulator 12 with respect to the mounting frame 11 rigidly connected with the patient 6 and thus, in the present example, the position of the tip of a biopsy needle from the position of the mounting frame 11 determined by imaging MR measurement and to display it to the surgeon via the display means 9 in the form of an MR tomogram of the investigated area of the patient 6 with faded-in needle position. In this connection, the tip of the needle may be faded into the MRI image e.g. as illuminated point, wherein the image may be a spatial three-dimensional representation or a two-dimensional slice image.

The MR measurable substance in the marking point 13 will generally contain protons, in particular water and may be present e.g. in the form of a gel in a corresponding encapsulation.

In order to avoid distortion of the MR recordings or an impairment of their image quality, the entire positioning system consists exclusively of non-magnetic materials. The display means 9 shown in FIG. 1 may comprise e.g. a special "solid state" screen having a LCD or TFT display, whereby it is possible to avoid the generation of disturbing RF fields and/or magnetic fields in the investigation volume 3 which would have a negative influence on the image quality.

FIG. 2 shows in a more detailed manner than FIG. 1 a stereo-tactic positioning system used with the inventive MR tomograph for the exact determination of the position of the manipulator 12, in particular e.g. a biopsy needle moved by the manipulator 12. A mounting frame 11 is shown which comprises a means for mechanically guiding the manipulator 12 in a spatial angular area, which comprises two rails 15, 15' on which the manipulator 12 can be moved by means of a sledge 16, in a manner simulating a gimbal suspension, on two circular arcs substantially perpendicular to one another.

Measuring means are provided to determine the respective spatial angular position of the manipulator 12 with respect to the mounting frame 11. There is also provided a device for determining the respective axial position of the manipulator 12 or a biopsy needle with respect to the mechanical guiding means. It is also possible to provide further marking means to determine the spatial position of the manipulator 12 with respect to the mounting frame 11 using e.g. mechanical, electrical, piezoelectrical or optical path length measurements. It is also possible to mechanically connect a marking point comprising MR measurable substance rigidly with the above-mentioned guiding means or to construct the guiding means such that it contains a substance in which MR measurable signals can be excited.

Figure 3:
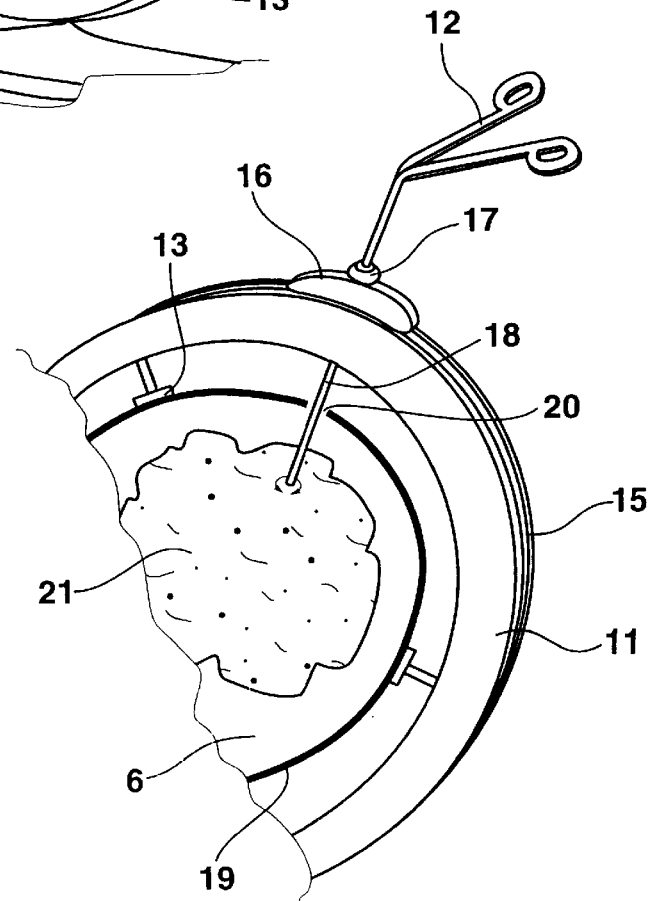
FIG. 3 a schematic horizontal sectional view through the indicated head of a patient with inserted biopsy needle and a manipulator suspended via a hinge.

The schematic sectional view of FIG. 3 shows part of the cranium 19 of a patient 6 who is to be operated on the brain 21 through a hole 20 in the cranium by means of a biopsy needle 18. In this connection, the manipulator 12, together with the biopsy needle 18, is moved via the sledge 16 on the rail 15 of the mounting frame 11 such that the relative position towards the area to be operated on, in particular the hole 20, is approximately reached. The manipulator 12 and thus also the biopsy needle 18 can be pivoted in a (usually small) range of solid angle by means of a ball joint 17 mounted on the sledge 16 in order to carry out fine adjustments of the position of the biopsy needle 18.

The sledge 16 contains means for measuring the spatial position of the manipulator 12 relative to the mounting frame 11. Measuring means are also provided for determining the location of frame member 15 relative to frame member 15'. These measuring means are mechanical, electrical, piezoelectrical and/or optical.

In order to be able to find the right path of the tip of the needle during an examination or operation, a certain point (e.g. within a tumor) is marked on the respective simultaneously generated MR image, which can be achieved preferably by means of a "mouse click" when a computer is used. The screen of the display means 9 then shows either numerically or preferably graphically the deviation of the actual position from the ideal position along the possible directions of displacement. The removed biopsy needle 18 is displaced on the two orthogonal circles until both deviations are minimized, e.g. until the optimum location for the hole 20 in the cranium 19 has been found. During subsequent insertion of the biopsy needle 18, the deviation is permanently displayed along said coordinate. It is preferred that these displays are faded in graphically, e.g. comparable with the "magic eye" which was common to radios in former times. In addition, it is possible to display the information also numerically and/or support it also acoustically.

I claim:

1. A positioning system for the exact determination of the position of a biopsy needle, relative to a measuring object, in particular the head, mamma or extremities of a patient, investigated by means of a magnetic resonance (MR) imaging measurement and located in an investigation volume of an MR tomograph, the MR tomograph having a magnet system for the generation of a homogenous magnetic field within the investigation volume and a gradient system for generating magnetic field gradient fields which vary linearly in the investigation volume, wherein the magnet system and the gradient system permit access to the investigation volume along at least two axes which intersect at an essentially right angle, the MR tomograph having a radio-frequency (RF) transmitting and receiving system for radiating RF pulses onto the measuring object and for receiving MR signals from the measuring object as well as an evaluation and display means for generating and displaying an MR image from inside the measuring object, the positioning system comprising:

a first frame component disposed on and without relative motion with respect to the measuring object;

a marking member disposed on said first frame component within the investigation volume in which the magnetic field is homogenous and the gradient fields are linear, said marking member comprising an MR substance in which measureable MR signals can be excited to define a position of said first frame component in the MR image via an imaging MR measurement;

a second frame component to which the biopsy needle is mounted, said second frame component movable relative to said first frame component;

movable mechanics disposed on said second frame component for moving the biopsy needle relative to said first frame component;

measuring means for determining a spatial position of the biopsy needle relative to said first frame component without using any MR signal; and means for displaying said spatial position in the MR image.

2. The positioning system of claim 1, further comprising evaluation means for determining a position of the biopsy needle in the MR image by calculation on the basis of said position of said first frame component determined by means of imaging MR measurement and said position of the biopsy needle relative to said first frame component determined by said measuring means without MR measurement.

3. The positioning system of claim 1, wherein said MR substance comprises protons.

4. The positioning system of claim 1, wherein said MR substance is a gel.

5. The positioning system of claim 2, wherein said measuring means effect a path length measurement using at least one of a mechanical member, an electrical member, a piezoelectrical member and an optical member.

6. The positioning system of claim 1, wherein said MR substance is rigidly connected to the measuring object.

7. The positioning system of claim 1, wherein said MR substance is rigidly connected to said first frame component.

8. The positioning system of claim 1, wherein the entire positioning system consists essentially of non-magnetic materials.

9. The positioning system of claim 1, wherein said movable mechanics comprises an angle member for mechanically guiding the biopsy needle within a range of solid angle and wherein said measuring means comprise means for determining an angular position of the biopsy needle.

10. The positioning system of claim 9, wherein said angle member comprises a ball joint.

11. The positioning system of claim 10, wherein the manipulator comprises a biopsy needle.

12. The positioning system of claim 9 wherein said movable mechanics effects two-dimensional motion in the manner of a gimbal mounting.

13. The positioning system of claim 1, wherein said movable mechanics displace the biopsy needle relative to said first frame component along two substantially circular and substantially mutually perpendicular arcs.

14. The positioning system of claim 1, wherein said movable mechanics comprise guiding means for moving the biopsy needle relative to said second frame component and said measuring means comprise means for determining an axial position of the biopsy needle relative to said guiding means.

15. A method for determining the exact position of a tip of a biopsy needle relative to a measuring object, in particular the head, mamma or extremities of a patient, investigated by means of a magnetic resonance (MR) imaging measurement and located in an investigation volume of a MR tomograph, the MR tomograph having a magnet system for the generation of a homogenous magnetic field within the investigation volume and a gradient system for generating magnetic gradient fields which vary linearly in the investigation volume, wherein the magnet system and the gradient system permit access to the investigation volume along at least two axes which intersect at an essentially right angle, the MR tomograph having a radio-frequency (RF) transmitting and receiving system for irradiating RF pulses onto the measuring object and for receiving MR signals from the measuring object as well as an evaluation and display means for generating and displaying an MR image from inside the measuring object, the method comprising the steps of:

a) disposing a first frame component on and without relative motion with respect to the measuring object, said first frame component having a marking member disposed on said first frame component within the investigation volume in which the magnetic field is homogenous and the gradient fields are linear, said marking member comprising an MR substance in which measurable MR signals can be excited;

b) moving the biopsy needle relative to said first frame component using a second frame component to which the biopsy needle is mounted, said second frame component being movable relative to said first frame component;

c) determining a spatial position of the biopsy needle relative to said first frame component without using any MR signal;

d) determining an absolute position of said first frame component using imaging MR measurements simultaneously during actuation of the biopsy needle and using measuring signals from said marking member; and e) displaying said spatial position of the biopsy needle in the image.

16. The method of claim 15, wherein a relative position of the biopsy needle with respect to said first frame component is determined repeatedly and simultaneously during actuation of the biopsy needle using at least one of mechanical, electrical, piezoelectrical and optical measuring signals.

17. The method of claim 15, wherein an absolute position of a certain section of said biopsy needle located within the measuring object is determined during manipulation by computer calculation and is faded into the MR image.

18. A method for guiding a tip of a biopsy needle to a predetermined point inside a measuring object, wherein the biopsy needle is guided on two circular arcs outside of the measuring object in a defined manner and can be displaced along an axis located essentially perpendicular to the circular arcs, the method comprising the steps of:

a) disposing a first frame component on and without relative motion with respect to the measuring object, said first frame component having a marking member disposed on said first frame component within the investigation volume in which the magnetic field is homogenous and the gradient fields are linear, said marking member comprising an MR substance in which measurable MR signals can be excited;

b) locating the biopsy needle outside of the measuring object;

c) displaying an MR image of the measuring object;

d) marking a desired position on said MR image;

e) determining, using evaluation and display means, optimum coordinates along the circular arcs and the axis;

f) fading permanently updated deviations from said optimum coordinates into the MR image;

g) manually minimizing said deviations through movement of said biopsy needle along the circular arc; and h) manually inserting said biopsy needle into the measuring object along the axis taking into consideration said permanently updated deviation until a tip of the biopsy needle is located at said desired position.

19. The method according to claim 18, further comprising assisting the graphic display with an acoustic display.

20. A positioning system for the exact determination of the position of a manually guided manipulator, in particular a tip of a biopsy needle, relative to a measuring object, in particular the head, mamma or extremities of a patient, investigated by means of a magnetic resonance (MR) imaging measurement and located in an investigation volume of an MR tomograph, the MR tomograph having a magnet system for the generation of a homogenous magnet field within the investigation volume and a gradient system for generating magnetic gradient fields which vary linearly in the investigation volume, wherein the magnet system and the gradient system permit access to the investigation volume along at least two axes which intersect at an essentially right angle, the MR tomograph having a radio frequency (RF) transmitting and receiving system for irradiating RF pulses onto the measuring object and for receiving MR signals from the measuring object as well as an evaluation and display means for generating and displaying an MR image from inside the measuring object, the positioning system comprising:

a first frame component disposed on and without relative motion with respect to the measuring object;

a marking member disposed on said first frame component within the investigation volume in which the magnetic field is homogenous and the gradient fields are linear, said marking member comprising an MR substance in which measureable MR signals can be excited to define a position of said first frame component in the MR image via an imaging MR measurement;

a second frame component to which the manipulator is mounted, said second frame component movable relative to said first frame component;

movable mechanics disposed on said second frame component for moving the manipulator relative to said first frame component;

measuring means for determining a spatial position of the manipulator relative to said first frame component without using any MR signal;

means for displaying said spatial position in the MR image, wherein said movable mechanics comprises an angle member for mechanically guiding the manipulator within a range of solid angle and wherein said measuring means comprise means for determining an angular position of the manipulator, wherein said angle member comprises a ball joint.

21. A positioning system for the exact determination of the position of a manually guided manipulator, in particular a tip of a biopsy needle, relative to a measuring object, in particular the head, mamma or extremities of a patient, investigated by means of a magnetic resonance (MR) imaging measurement and located in an investigation volume of a MR tomograph, the MR tomograph having a magnet system for the generation of a homogenous magnetic field within the investigation volume and a gradient system for generating magnetic gradient fields which vary linearly in the investigation volume, wherein the magnet system and the gradient system permit access to the investigation volume along at least two axes which intersect at an essentially right angle, the MR tomograph having a radio-frequency (RF) transmitting and receiving system for radiating RF pulses onto the measuring object and for receiving MR signals measuring means for determining a spatial position of the manipulator relative to said first frame component without using any MR signal;

means for displaying said spatial position in the MR image, wherein said movable mechanics comprises an angle member for mechanically guiding the manipulator within a range of solid angle and wherein said measuring means comprise means for determining an angular position of the manipulator, wherein said angle member comprises a ball joint.

* * * * *